US009109987B2

(12) United States Patent
Kinugasa

(10) Patent No.: US 9,109,987 B2
(45) Date of Patent: Aug. 18, 2015

(54) PARTICLE DETECTING DEVICE AND PARTICLE DETECTING METHOD

(71) Applicant: Azbil Corporation, Tokyo (JP)

(72) Inventor: Seiichiro Kinugasa, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 0 days.

(21) Appl. No.: 14/562,999

(22) Filed: Dec. 8, 2014

(65) Prior Publication Data

US 2015/0160112 A1    Jun. 11, 2015

(30) Foreign Application Priority Data

Dec. 10, 2013 (JP) ................................. 2013-255274

(51) Int. Cl.

| G01T 1/20 | (2006.01) |
|---|---|
| G01N 15/02 | (2006.01) |
| G01N 21/64 | (2006.01) |
| G01J 3/44 | (2006.01) |
| G01N 15/00 | (2006.01) |
| G01N 21/00 | (2006.01) |
| G01N 21/3554 | (2014.01) |
| G01N 21/35 | (2014.01) |

(52) U.S. Cl.
CPC ........... *G01N 15/0211* (2013.01); *G01J 3/4406* (2013.01); *G01J 3/4412* (2013.01); *G01N 21/6486* (2013.01); *G01N 2021/6417* (2013.01)

(58) Field of Classification Search
CPC ....... G01N 15/00; G01N 21/00; G01N 21/35; G01N 21/3554; G01J 3/4406; G01J 3/4412; G01T 1/20

See application file for complete search history.

(56) References Cited

U.S. PATENT DOCUMENTS

2008/0074662 A1* 3/2008 Gu et al. ........................ 356/301

FOREIGN PATENT DOCUMENTS

| JP | 2011-083214 | 4/2011 |
|---|---|---|
| JP | 2013-117466 | 6/2013 |

OTHER PUBLICATIONS

Norio Hasegawa, et al., "Instantaneous Bioaerosol Detection Technology and Its Application", azbil Technical Review, Yamatake Corporation, pp. 2-7, Dec. 2009.

* cited by examiner

*Primary Examiner* — David Porta
*Assistant Examiner* — Faye Boosalis
(74) *Attorney, Agent, or Firm* — Troutman Sanders LLP

(57) ABSTRACT

A particle detecting device includes: a fluorescence measuring instrument that measures light in a fluorescent band, which is produced in a region that is illuminated by an excitation beam from a light source; and an evaluating portion that evaluates whether the light measured by the fluorescence measuring instrument includes Raman-scattered light and florescent light, to evaluate that a fluorescent particle is included in the fluid if the evaluation is that the measured light includes florescent light, and to evaluate that the fluid does not include a fluorescent particle if the evaluation is that the measured light does not include fluorescent light, to evaluate that moisture is included in the fluid if there is an evaluation that the measured light includes Raman scattered light, and to evaluate that the fluid does not include moisture if there is an evaluation that the measured light does not include Raman scattered light.

20 Claims, 7 Drawing Sheets

PARTICLE DETECTING DEVICE AND PARTICLE DETECTING METHOD

CROSS REFERENCE TO RELATED APPLICATION

This application claims priority under 35 U.S.C. §119 to Japanese Patent Application No. 2013-255274, filed on Dec. 10, 2013, the entire content of which being hereby incorporated herein by reference.

FIELD OF TECHNOLOGY

The present disclosure relates to an environment evaluating technology, and, in particular, relates to a particle detecting device and particle detecting method.

BACKGROUND

In clean rooms, such as bio clean rooms, airborne microorganism particles and non-microorganism particles are detected and recorded using particle detecting devices. See, for example, Japanese Unexamined Patent Application Publication 2011-83214 and N. Hasegawa, et al., *Instantaneous Bioaerosol Detection Technology and Its Application*, azbil Technical Review, 2-7, Yamatake Corporation, December 2009. The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. When there is a microorganism or a non-microorganism particle included within the air, a particle that is illuminated with light emits fluorescence, enabling detection of the numbers, sizes, and the like, of microorganisms and non-microorganism particles included in the air. Moreover, there is the need for technologies for accurately detecting particles in a fluid outside of clean rooms as well. See, for example, Japanese Unexamined Patent Application Publication 2013-117466.

However, when a substance that emits light in the fluorescent range but that is not a fluorescent particle that is the subject of detection is included in the fluid, such as air, that is to be inspected, then in some cases the particle detecting device may incorrectly detect this substance as a fluorescent particle that is the subject of detection. Given this, an aspect of the present invention is to provide a particle detecting device and particle detecting method able to detect accurately the fluorescent particles that are the subjects of detection.

SUMMARY

An example of the present disclosure provides:
(a) a light source that illuminates a fluid with an excitation beam;
(b) a fluorescence measuring instrument that measures light in a fluorescent band, which is produced in a region that is illuminated by the excitation beam; and
(c) an evaluating portion that evaluates whether or not the light that is measured by the fluorescence measuring instrument includes Raman-scattered light and florescent light, to evaluate that a fluorescent particle is included in the fluid if the evaluation is that the measured light includes florescent light, and to evaluate that the fluid does not include a fluorescent particle if the evaluation is that the measured light does not include fluorescent light, to evaluate that moisture is included in the fluid if there is an evaluation that the measured light includes Raman scattered light, and to evaluate that the fluid does not include moisture if there is an evaluation that the measured light does not include Raman scattered light,
(d) the above (a)-(c) provided in a structure of a particle detecting device. Note that a "fluid" includes "gases" and "liquids." Note also that "fluorescent light" includes auto fluorescent light.

Moreover, another example of the present disclosure provides:
(a) illumination of a fluid with an excitation beam;
(b) measurement of light in a fluorescent band, which is produced in a region that is illuminated by the excitation beam; and
(c) evaluation of whether or not the light that is measured by the fluorescence measuring instrument includes Raman-scattered light and florescent light, to conclude that a fluorescent particle is included in the fluid if the evaluation is that the measured light includes florescent light, and to conclude that the fluid does not include a fluorescent particle if the evaluation is that the measured light does not include fluorescent light, to evaluate that moisture is included in the fluid if there is an evaluation that the measured light includes Raman scattered light, and to conclude that the fluid does not include moisture if there is an evaluation that the measured light does not include Raman scattered light.

The present disclosure enables the provision of a particle detecting device and particle detecting method wherein fluorescent particles, which are the particles that are subject to detection, can be detected accurately.

BRIEF DESCRIPTIONS OF THE DRAWINGS

DETAILED DESCRIPTION

Examples of the present disclosure will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Figure 1:
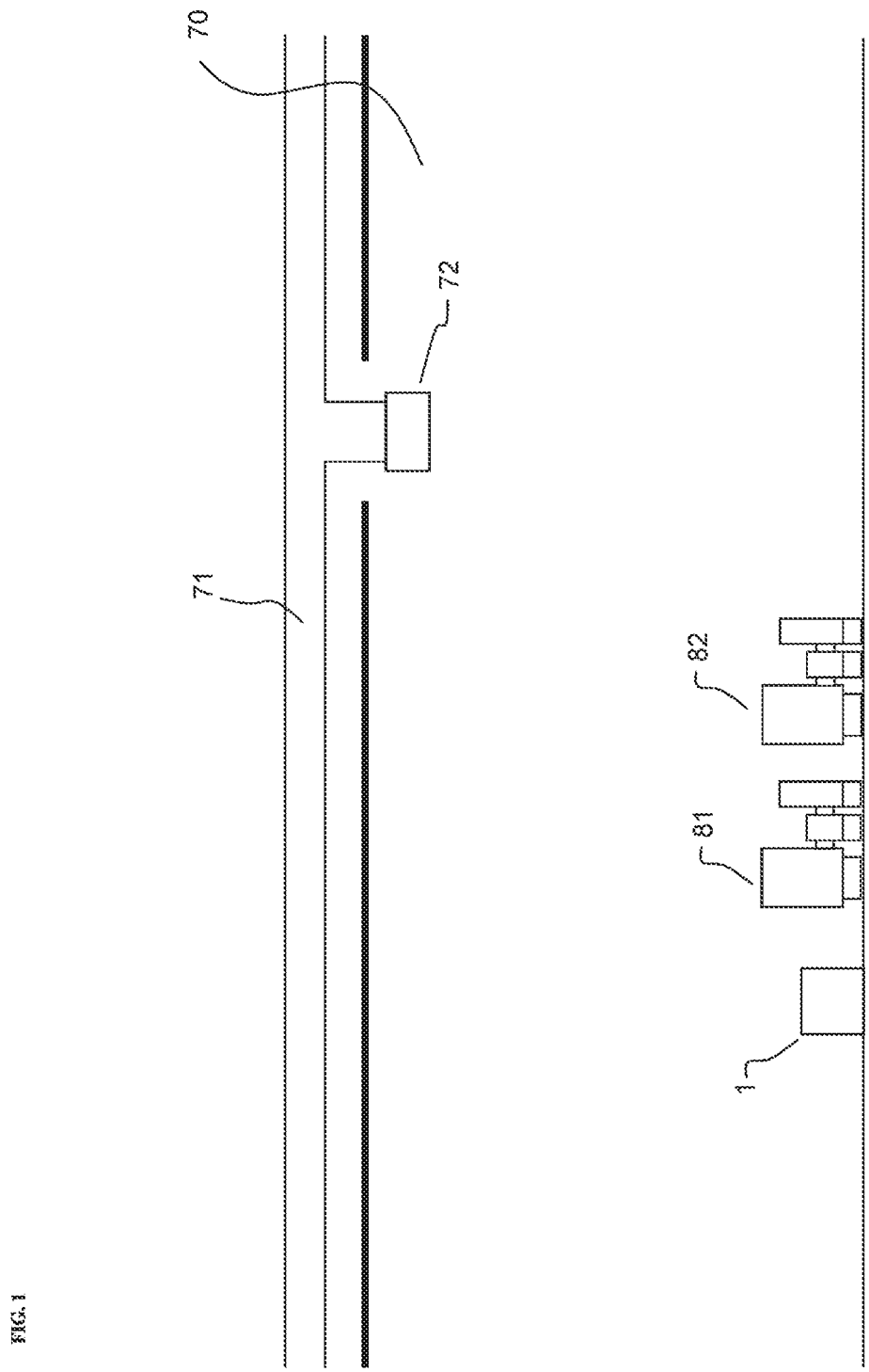
FIG. 1 is a schematic diagram of a clean room according to an example according to the present disclosure.

As illustrated in FIG. 1, a particle detecting device 1 according to the present example is disposed in, for example, a clean room 70. In the clean room 70, clean air is blown in through a duct 71 and through a blowing opening 72 having an ultrahigh performance air filter such as a HEPA filter (High Efficiency Particulate Air Filter) or ULPA filter (Ultra Low Penetration Air Filter), or the like.

Manufacturing lines 81 and 82 are arranged inside of the clean room 70. The manufacturing lines 81 and 82 are manufacturing lines, for, for example, precision instruments, electronic components, or semiconductor devices. Conversely, the manufacturing lines 81 and 82 may be manufacturing lines for foodstuffs, beverages, or pharmaceuticals. For example, in the manufacturing lines 81 and 82, an infusion liquid may be filled into an intravenous infusion device or a hypodermic. Conversely, the manufacturing lines 81 and 82 may manufacture oral medications or Chinese herb medications. On the other hand, the manufacturing lines 81 and 82 may fill containers with a vitamin drink or beer. If a beverage is manufactured within a clean room 70, then the interior of the clean room 70 may be maintained at high humidity. Moreover, in some cases the air within the clean room 70 is subjected to steam sterilization, and includes a great deal of moisture.

The manufacturing lines 81 and 82 normally are controlled so that microorganism particles and non-microorganism particles, and the like, are not dispersed into the air within the clean room 70. However, manufacturing lines 81 and 82, for some reason, are sources that produce microorganism particles and non-microorganism particles that become airborne in the clean room 70. Moreover, factors other than the manufacturing lines 81 and 82 also disperse microorganism particles and non-microorganism particles into the air of the clean room 70.

Examples of microorganism particles that may become airborne in the clean room 70 include microbes. Examples of such microbes include Gram-negative bacteria, Gram-positive bacteria, and fungi such as mold spores. *Escherichia coli*, for example, can be listed as an example of a Gram-negative bacterium. *Staphylococcus epidermidis, Bacillus atrophaeus, Micrococcus lylae*, and *Corynebacterium afermentans* can be listed as examples of Gram-positive bacteria. *Aspergillus niger* can be listed as an example of a fungus such as a mold spore. However, the microorganism particles that may become airborne in the clean room 70 are not limited to these specific examples. Examples of non-microorganism particles that may become airborne in the clean room 70 include splashed chemical substances, pharmaceuticals, or foodstuffs, along with dust, dirt, grime, and the like.

If a microorganism particle is illuminated with light, the nicotinamide adenine dinucleotide (NADH) and the flavins, and the like, that are included in microorganism particle produce fluorescent light. The wavelength of the fluorescence that derives from NADH is in the neighborhood of 480 nm. Moreover, the wavelength of the fluorescence that derives from flavins is in the neighborhood of 530 nm. However, fluorescent particles that fall off of a gown, made from polyester, for example, that has been cleaned will emit fluorescence when illuminated with light. Moreover, polystyrene particles also emit fluorescence, and then fade. Consequently, conventionally, particle detecting devices have identified the existence of fluorescent particles that are subjects to be detected within the air by illuminating the air with an excitation beam and detecting the fluorescence. Note that "fluorescent light" includes autofluorescent light.

Figure 2:
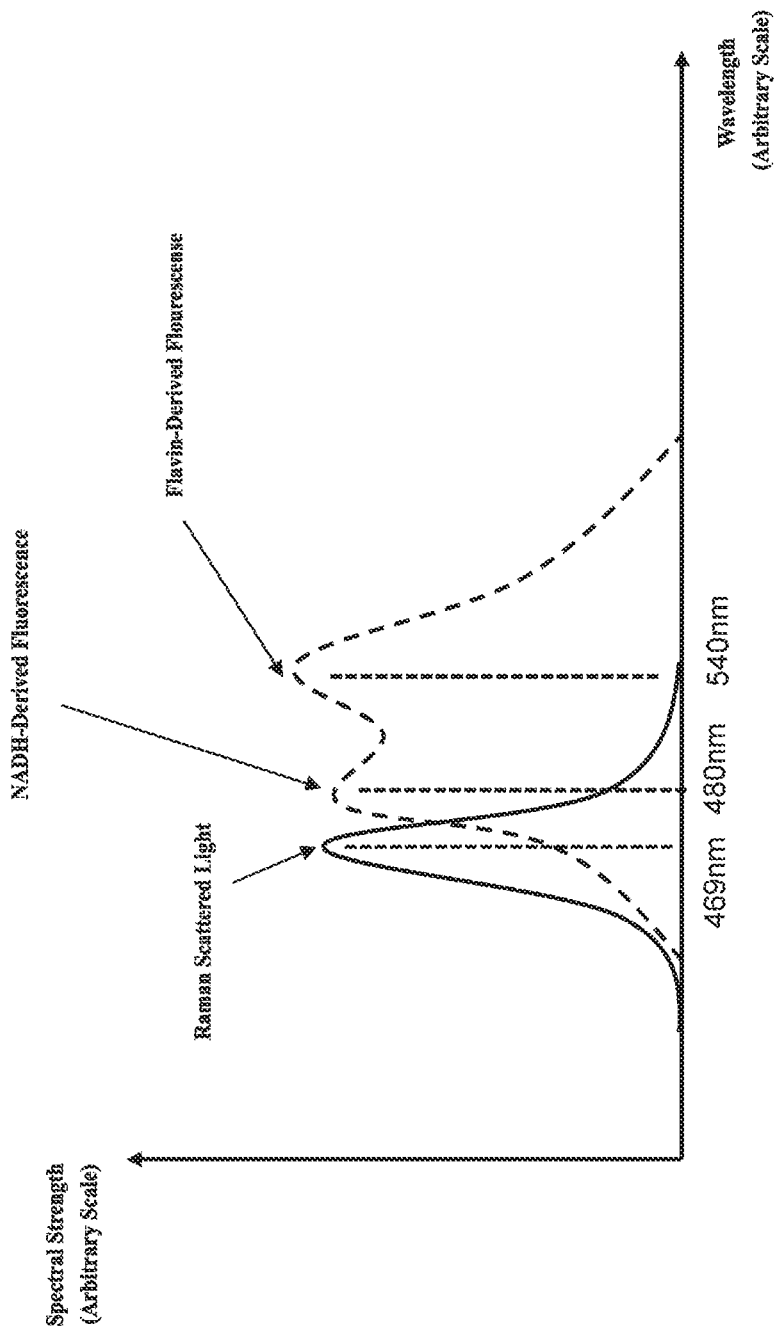
FIG. 2 is spectra for Raman-scattered light and fluorescence according to an example according to the present disclosure.

Even if fluorescent particles that emit fluorescence, as described above, are not included within the air, still, if there is moisture in the air, such as water vapor, then the moisture that is illuminated by excitation beam such as ultraviolet radiation will produce Raman scattered light (inelastic scattered light). The wavelength of the Raman scattered light is in the neighborhood of 460 nm, which, as illustrated in FIG. 2, is near to the wavelength of fluorescence deriving from NADH. Because, in this way, the Raman scattered light has a wavelength band that overlaps that of fluorescence, the particle detecting device will detect Raman light as light in the fluorescent band. Consequently, the conventional particle detecting device, when detecting Raman scattered light, may incorrectly evaluate that a microorganism particle that includes NADH, or a non-microorganism particle that emits fluorescence in the vicinity of a wavelength of 460 nm, is present.

Figure 3:
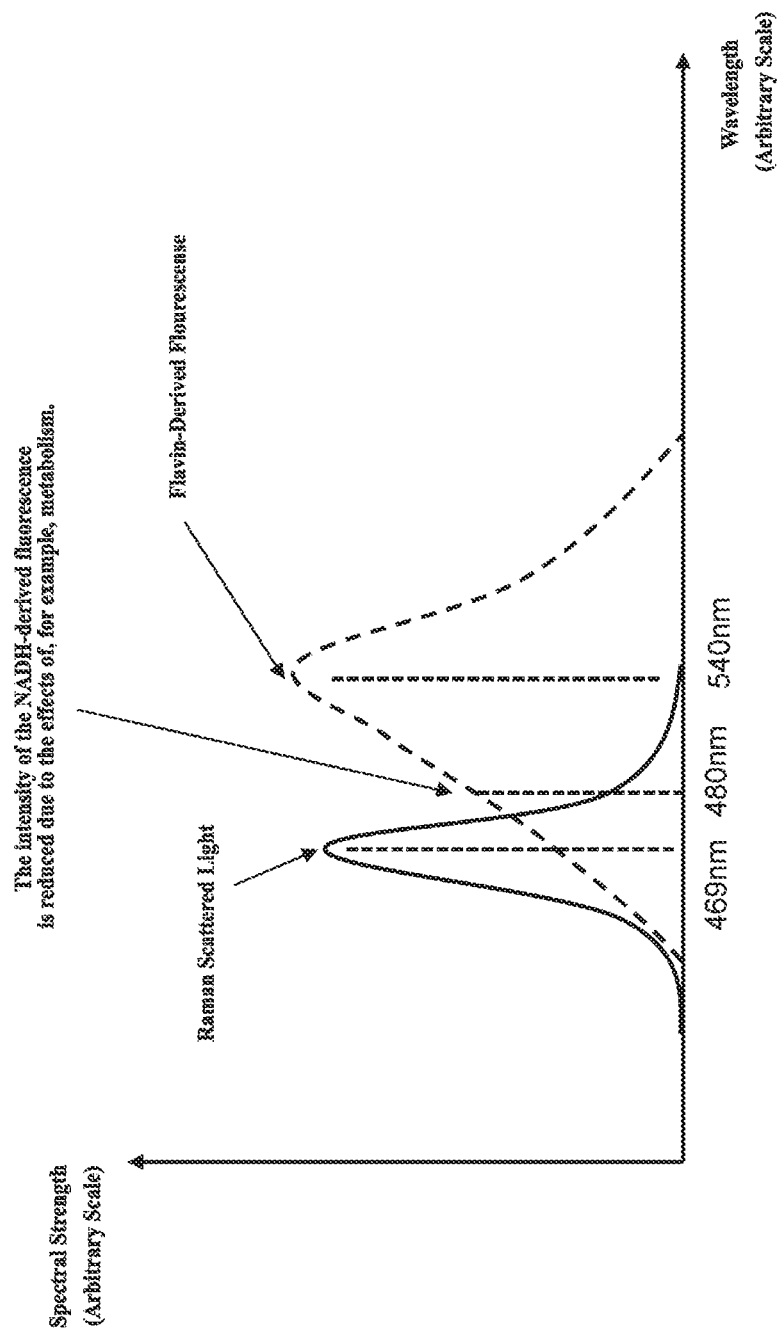
FIG. 3 is spectra for Raman-scattered light and fluorescence according to an example according to the present disclosure.

Moreover, as illustrated in FIG. 3, there are also cases wherein the effects of metabolism by the microorganism may decrease the intensity of the fluorescence that derives from NADH. In contrast, the intensity of the fluorescence that derives from flavins tends to be resistant to the effects of microorganism metabolism.

Figure 4:
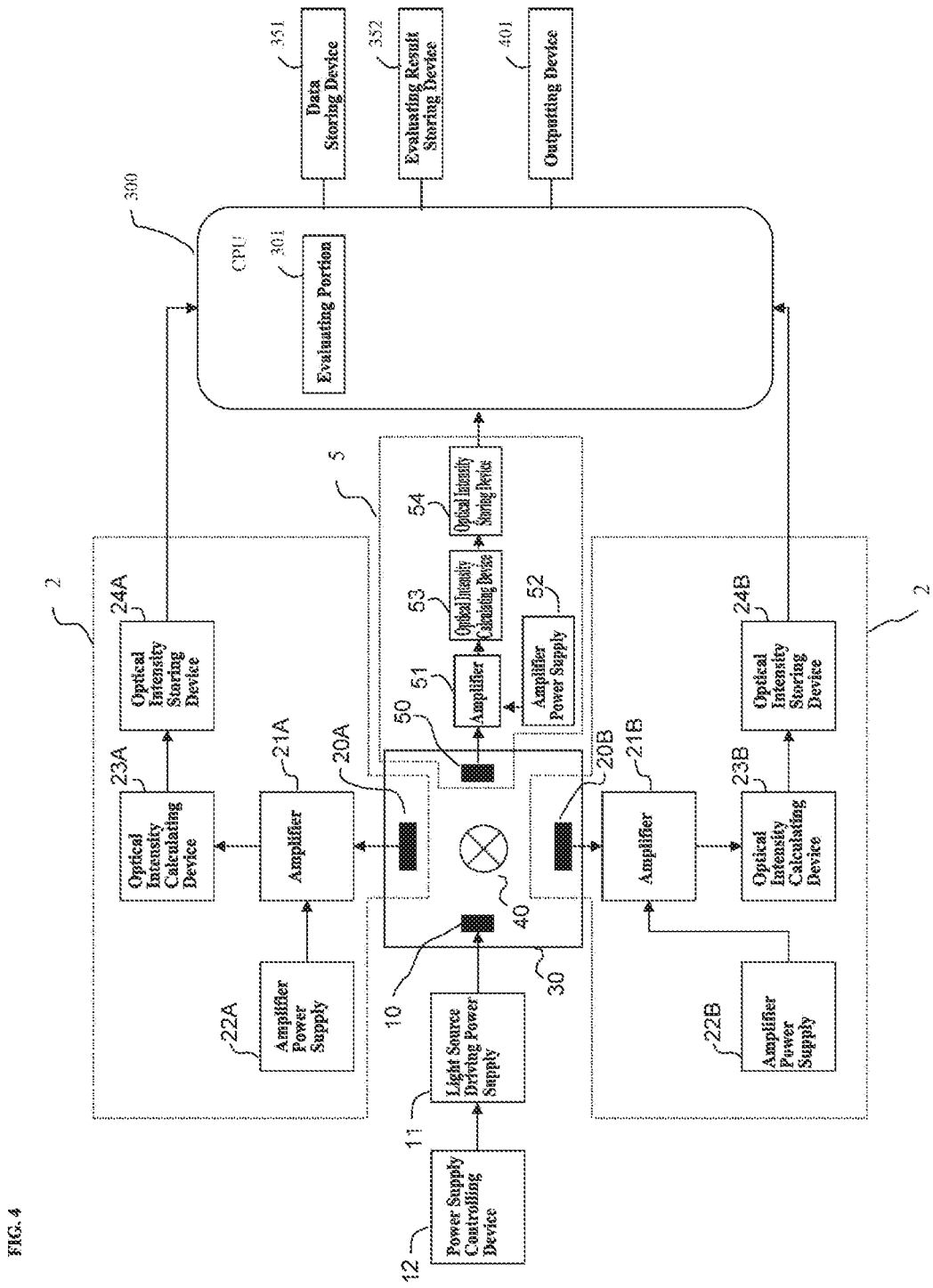
FIG. 4 is a schematic diagram of a particle detecting device according to an example according to the present disclosure.

Here, as illustrated in FIG. 4, the particle detecting device 1 according to the present example includes a light source 10 that directs an excitation beam into a fluid, a fluorescence measuring instrument 2 that measures, at a plurality of wavelengths, the intensities of light in the fluorescent band that are produced in the region that is illuminated by the excitation beam, and a Mie scattered light measuring instrument 5 that measures the scattered light that is produced in the region that is illuminated by the excitation beam. The light source 10, the fluorescence measuring instrument 2, and the Mie scattered light measuring instrument 5 are connected electrically to the central calculation processing device (CPU) 300.

The CPU 300 includes an evaluating portion 301 for evaluating whether or not the light that is measured by the fluorescence measuring instrument 2 includes Raman scattered light and florescent light. When the evaluating portion 301 evaluates that the measured light includes fluorescence, it evaluates that the fluid includes a fluorescent particle, and when it evaluates that the measured light does not include fluorescence, it evaluates that the fluid does not include a fluorescent particle. Moreover, when the evaluating portion 301 evaluates that the measured light includes Raman scattered light, it evaluates that the fluid includes moisture, and when it evaluates that the measured light does not include Raman scattered light, then it concludes that the fluid does not include moisture.

While in the present example the explanation is for an example wherein the fluid that is subject to inspection is air and wherein the fluorescent particle that is subject to detection is a microorganism particle that includes NADH and flavins, the examples of the present invention are not limited thereto.

The light source 10, the fluorescence measuring instrument 2, and the Mie scattered light measuring instrument 5 are provided in a frame 30. A light source driving power supply 11, for supplying electric power to the light source 10, is connected to the light source 10. A power supply controlling device 12, for controlling the electric power that is supplied to the light source 10, is connected to the light source driving power supply 11. The particle detecting device 1 further includes a first suction device that draws the air, into the frame 30 that is illustrated in FIG. 4, from within the clean room 70, illustrated in FIG. 1. The air that is drawn in by the first suction device is expelled from the tip end of a nozzle 40 of the flow path within the frame 30. The air that is emitted from the tip end of the nozzle 40 is drawn in by a second section device that is disposed within the frame 30, facing the tip end of the nozzle 40.

The light source 10 emits an excitation beam of a wide wavelength band towards the gas flow of the air that is expelled from the tip end of the nozzle 40 and drawn into the second suction device. A light-emitting diode (LED) or a laser may be used for the light source 10. The wavelength of the excitation beam is, for example, between 250 and 550 nm. The excitation beam may be of visible light, or of ultraviolet light. If the excitation beam is of visible light, then the wavelength of the excitation beam is within a range of, for example, 400 to 550 nm, for example, 405 nm. If the excitation beam is ultraviolet radiation, then the wavelength of the excitation beam is in a range of, for example, between 300 and 380 nm, for example, 340 nm. However, the wavelength of the excitation beam is not limited to these.

If a microorganism particle, such as a bacterium, or the like, is included in the gas flow that is expelled from the nozzle 40, the microorganism particle, illuminated by the excitation beam, emits fluorescence. Moreover, even in a case wherein a non-microorganism particle, such as a polyester particle, is included in the gas flow that is expelled from the nozzle 40, the non-microorganism particle that is illuminated by the excitation beam will emit fluorescence. Moreover, when moisture is included in the gas flow that is expelled from the nozzle 40, then Raman scattered light that is light in the fluorescent band will be produced in the moisture that is illuminated by the excitation beam.

The Mie scattered light measuring instrument 5 measures the Mie scattered light that is produced by particles that include moisture. The Mie scattered light measuring instrument 5 is provided with a scattered light detecting element 50 for detecting scattered light. A photodiode, or the like, may be used for the scattered light detecting element 50, where, when light is received, the optical energy is converted into electrical energy. An amplifier 51, for amplifying the electric current that is produced by the scattered light detecting element 50 is connected to the scattered light detecting element 50. An amplifier power supply 52, for supplying electric power to the amplifier 51, is connected to the amplifier 51. Furthermore, an optical intensity calculating device 53, for receiving the electric current that has been amplified by the amplifier 51, to calculate the intensity of the scattered light that has been received by the scattered light detecting element 50, is connected to the amplifier 51. An optical intensity storing device 54, for storing the intensity of the scattered light, calculated by the optical intensity calculating device 53, is connected to the optical intensity calculating device 53.

The fluorescence measuring instrument 2 measures the light in the fluorescent band emitted by the microorganism particles that are subjects to be detected, and from the non-microorganism particles. The fluorescence measuring instrument 2 includes a first photodetecting element 20A that detects light in the fluorescent band at a first wavelength, and a second photodetecting element 20B that detects light of a fluorescent band at a second wavelength that is different from the first wavelength. Note that the "first wavelength" may have a band. The same is true for the second wavelength. A photodiode, a photoelectron tube, or the like may be used for the first photodetecting element 20A and the second photodetecting element 20B, to convert the photonic energy into electric energy when the light is detected.

An amplifier 21A that amplifies the current that is produced by the first photodetecting element 20A is connected to the first photodetecting element 20A. An amplifier power supply 22A, that supplies electric power to the amplifier 21A, is connected to the amplifier 21A. Moreover, an optical intensity calculating device 23A, for calculating the intensity of the light detected by the first photodetecting element 20A, by detecting the current that has been amplified by the amplifier 21A, is connected to the amplifier 21A. An optical intensity storing device 24A, for storing the optical intensity calculated by the optical intensity calculating device 23A, is connected to the optical intensity calculating device 23A.

An amplifier 21B for amplifying the current that is produced by the second photodetecting element 20B is connected to the second photodetecting element 20B. An amplifier power supply 22B, for supplying electric power to the amplifier 21B, is connected to the amplifier 21B. Moreover, an optical intensity calculating device 23B, for calculating the intensity of the light detected by the second photodetecting element 20B, by detecting the current that has been amplified by the amplifier 21B, is connected to the amplifier 21B. An optical intensity storing device 24B, for storing the optical intensity calculated by the optical intensity calculating device 23B, is connected to the optical intensity calculating device 23B. Note that while in FIG. 4 an example is shown wherein the fluorescence measuring instrument 2 is provided with first and second photodetecting elements 20A and 20B, the fluorescence measuring instrument 2 may be provided with a greater number of photodetecting elements instead, to measure the intensities of light at a plurality of other wavelengths in the fluorescent band as well.

The evaluating portion 301 calculates the spectral center of mass based on the intensities of light in the fluorescent band at the plurality of wavelengths. Additionally, the evaluating portion 301 calculates an optical spectrum in the fluorescent band that is produced in the region that is illuminated by the excitation beam. The evaluating portion 301 evaluates, based on the spectrum that is calculated, whether or not the light that has been measured by the fluorescence measuring instrument 2 includes Raman scattered light and florescent light. For example, the evaluating portion 301 compares the calculated spectrum to a spectrum for Raman scattered light, obtained in advance, and to a spectrum of fluorescent light derived from flavins, obtained in advance, to evaluate whether or not the light that is measured by the fluorescence measuring instrument 2 includes Raman scattered light and florescent light. The spectrum, obtained in advance, for Raman scattered light and a spectrum, obtained in advance, for fluorescent light deriving from flavins are, for example, stored in a data storing device 351 that is connected to the CPU 300.

Figure 5:
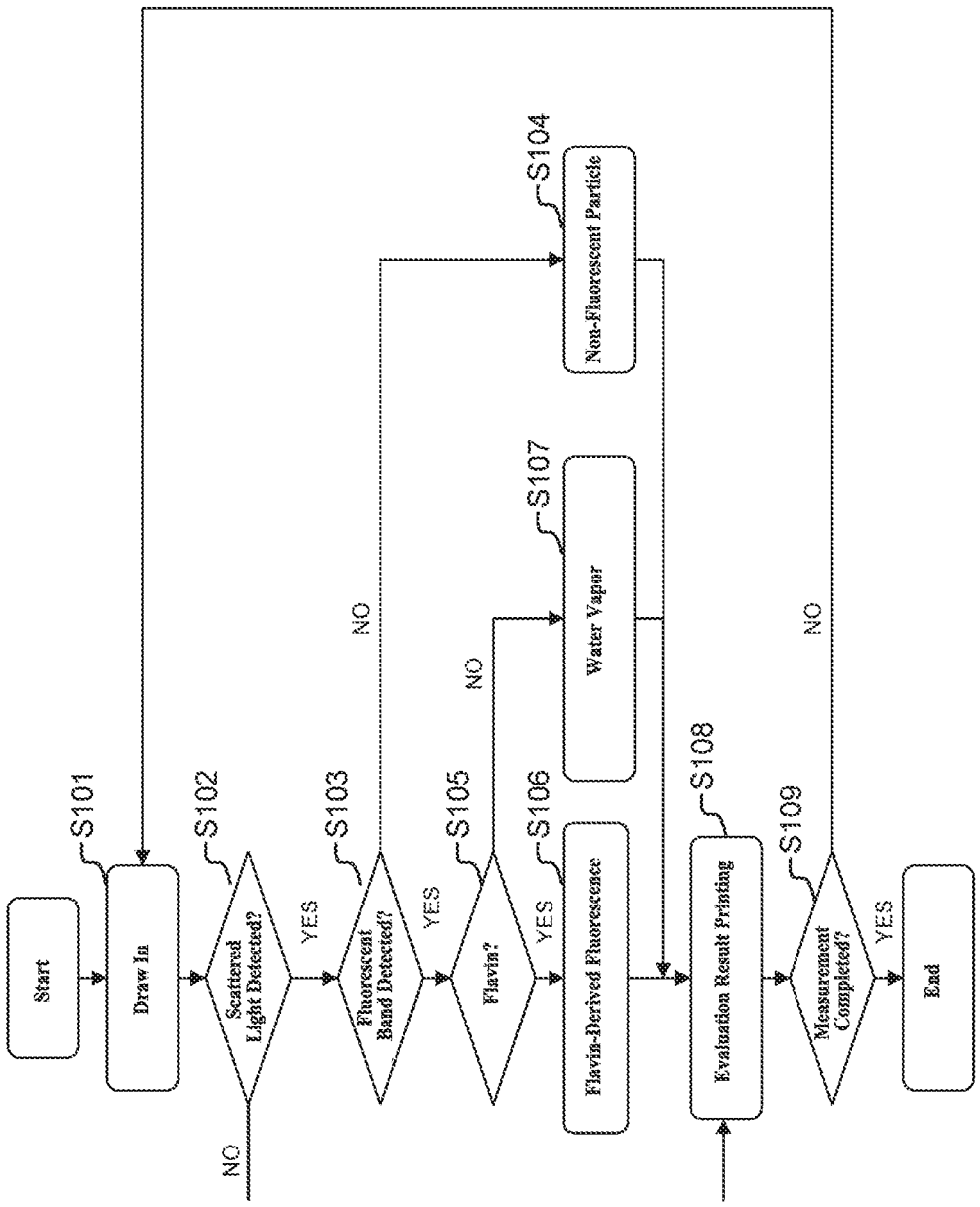
FIG. 5 is a flowchart illustrating a particle detecting method as set forth in a example according to the present disclosure.

In Step S101 in FIG. 5, when air with an unknown included substance is drawn from the clean room 70 into the particle detecting device 1, illustrated in FIG. 1, the light source 10, illustrated in FIG. 4, directs an excitation beam into the air that is drawn in, and if, in Step S102, the Mie scattered light measuring instrument 5 measures Mie scattered light, then the optical intensity of the Mie scattered light is stored in the optical intensity storing device 54. The evaluating portion 301 reads out the intensity of the scattered light from the optical intensity storing device 54. If Mie scattered light has been measured, then the evaluating portion 304 concludes that a particle is included in the air that is the subject of the testing, and processing advances to Step S103. If no Mie scattered light is measured, then the evaluating portion 301 concludes that no particle is included in the air that is being tested, and processing advances to Step S108.

In Step S103, when the fluorescence measuring instrument 2 has measured the intensity of light in the fluorescent band at the first wavelength and measured the intensity of light in the fluorescent band in the second wavelength, the fluorescent intensities in the fluorescent bands are stored in the optical intensity storing devices 24A and 24B. If intensities of light in the fluorescent band in additional wavelengths are measured, the measured intensities are stored in the optical intensity storing device accordingly. The evaluating portion 301 reads out, from the optical intensity storing devices 24A and 24B, the value for the intensity of light in the fluorescent band at the first wavelength, the value for the intensity of light in the fluorescent band for the second wavelength, and, if necessary, the values for the intensities of fluorescent light in the other wavelengths. When the light in the fluorescent band has been measured, then the evaluating portion 301 evaluates that there is a fluorescent particle in the air that is being tested, and processing advances to Step S105. If light of a fluorescent band is not detected, then the evaluating portion 301, in Step S104, concludes that no fluorescent particle is included in the air that is being tested, but rather that a non-fluorescent particle is included, and processing advances to Step S108.

In Step S106, the evaluating portion 301 estimates the spectrum for the light in the fluorescent band from the intensities of light in the fluorescent band at the plurality of wavelengths. Furthermore, the evaluating portion 301 evaluates whether or not the estimated spectrum includes the fluorescent spectrum that derives from flavins or a flavin scattered light spectrum. In this evaluation, a prescribed threshold value may also be received. If the estimated spectrum includes a fluorescent spectrum that derives from flavin, and does not include a spectrum of Raman scattered light, then, in Step S106, the evaluating portion 301 evaluates that the air that is being tested includes microorganism particles that contain little moisture, and processing advances to Step S108.

If the estimated spectrum includes both the florescent spectrum that is derived from flavin and the Raman scattered light, then, in Step S106, the evaluating portion 301 concludes that the air that is being tested includes a microorganism that includes a large moisture content, such as *Escherichia coli*, or the like, and processing advances to Step S108. If the estimated spectrum includes the spectrum of Raman scattered light but does not include the fluorescent spectrum that derives from flavins, then, in Step S107, the evaluating portion 301 concludes that the gas that is being tested includes moisture but does not include a microorganism, and processing advances to Step S108.

In Step S108, the evaluating portion 301 stores the evaluation result into the evaluation result storing device 352, and outputs it to an outputting device 401 such as a display, a printer, or the like. In Step S109, the evaluating portion 301 evaluates whether or not the measurement has been completed. If the measurement is to be continued, then processing returns to Step S101.

Microorganisms normally include NADH and flavins. However, because the wavelength band of the fluorescent light that derives from NADH and the wavelength band of the Raman scattered light are close to each other, when it evaluating, based on the presence or absence of fluorescent light derived from NADH, whether or not there is a microorganism in the fluid that is being tested, if the Raman scattered light is detected then this may be incorrectly identified as having detected fluorescent light that derives from NADH that is included in a microorganism. Moreover, the intensity of the fluorescent light that derives from NADH is susceptible to the effects of metabolism of the microorganism. In addition, when there is an increase in the amount of amino acid molecules so that the density extinguishes the light, then the Raman scattered light will become relatively strong when compared to the fluorescent light.

In contrast, if the evaluation as to whether or not there is a microorganism in the fluid that is being tested is performed based on whether or not there is fluorescence that derives from flavins, which have a wavelength band that is distinct from the wavelength band of the Raman scattered light, then it is possible to evaluate accurately whether or not there is a microorganism, even if there is moisture in the fluid, producing Raman scattered light. Moreover, the intensity of the fluorescence that derives from flavins is relatively unaffected by the metabolism of the microorganism.

Conventionally methods have been proposed for measuring whether or not there is fluorescent light derived from microorganism particles through positioning a filter in front of the fluorescence measuring instrument in order to cut the Raman scattered light. However, when detecting microorganism particles that have a large amount of moisture content, such as *Escherichia coli*, or the like, then detecting both the Raman scattered light that is produced by the moisture content included in the microorganism and the fluorescent light deriving from the flavins enables a more precise evaluation as to whether or not there are microorganism particles.

Modified Example

Figure 6:
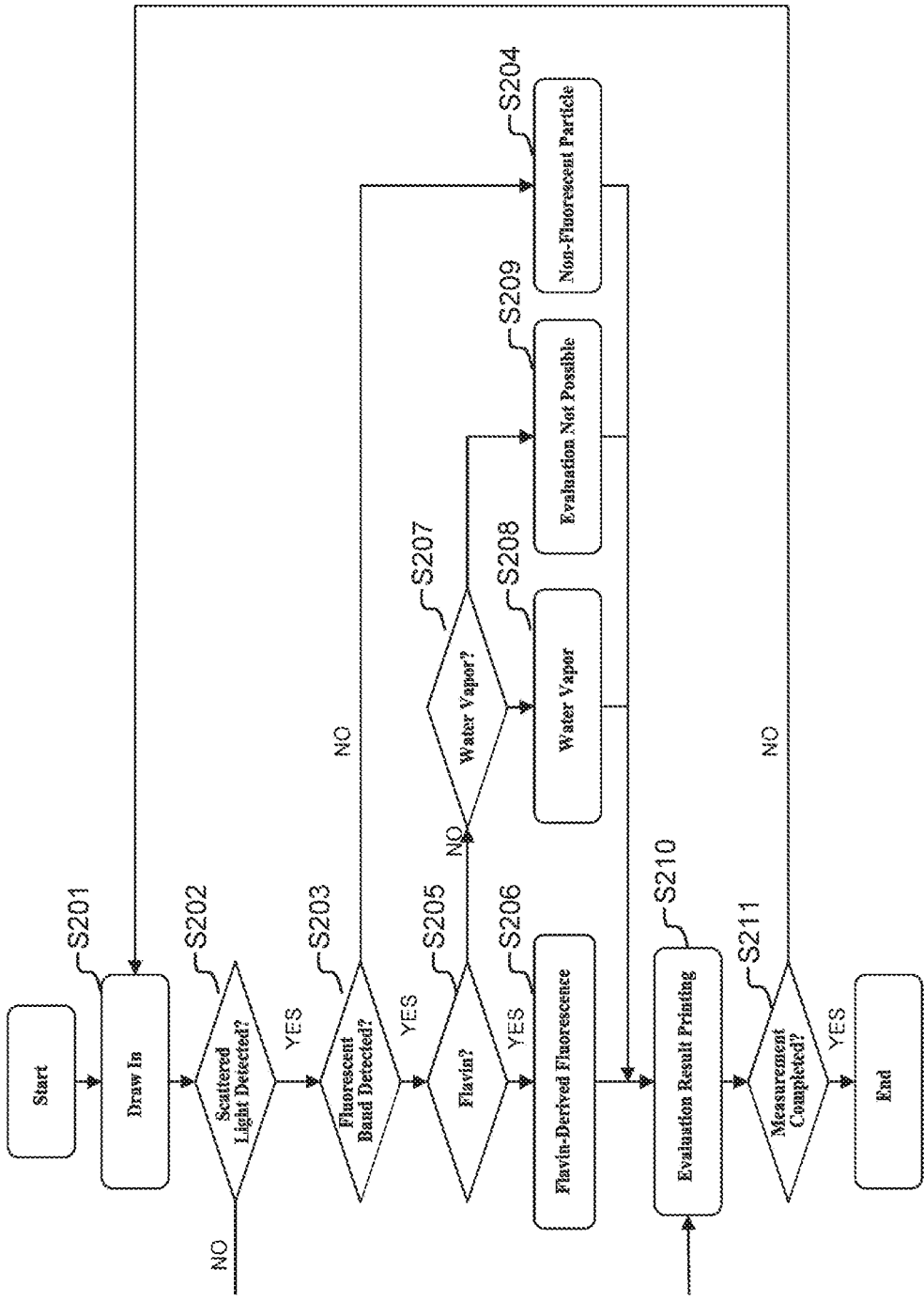
FIG. 6 is a flowchart illustrating a particle detecting method as set forth in a modified example according to the present disclosure.

The evaluating portion 301 may evaluate the presence or absence and type of particles using the method illustrated in FIG. 6. Step S201 through Step S206 in FIG. 6 are identical to Step S101 through Step S106 in FIG. 5. In Step S207, the evaluating portion 307 evaluates whether or not the estimated spectrum, which is an estimated spectrum that does not include the fluorescent spectrum deriving from flavin, includes the spectrum for the Raman scattered light. If the spectrum of the Raman scattered light is included, then processing advances to Step S208, and the evaluation is that the gas that is being tested includes moisture. If the estimated fluorescent band spectrum does not include the flavin-derived fluorescent spectrum and the Raman scattered light spectrum, then, in Step S209, the evaluating portion 301 determines that it is not possible to evaluate the type of particle that is included in the gas that is being tested. Step S210 and Step S211 are identical to Step S108 and Step S109 in FIG. 5.

Another Modified Example

Figure 7:
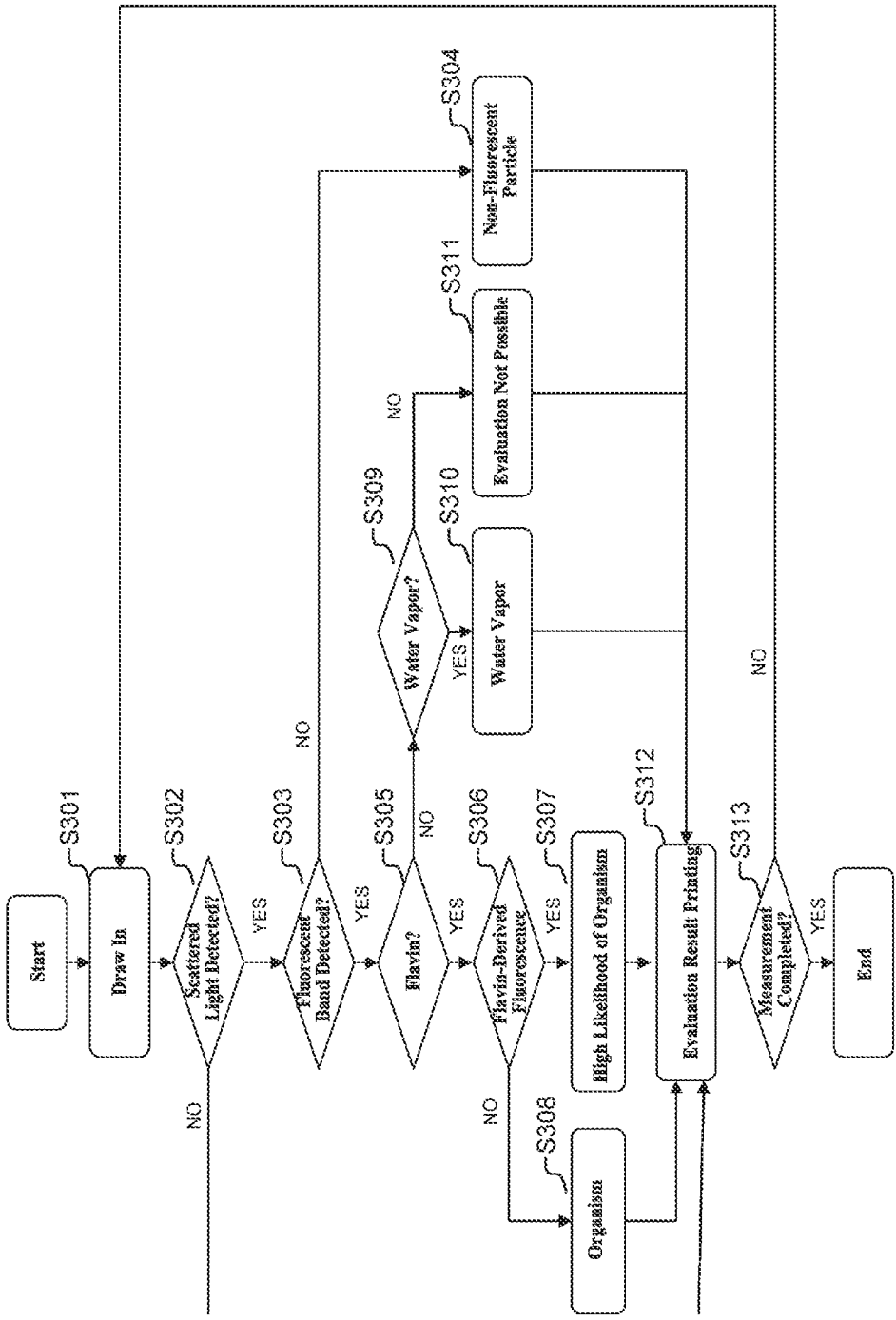
FIG. 7 is a flowchart illustrating a particle detecting method as set forth in another modified example according to the present disclosure.

The evaluating portion 301 may evaluate the presence or absence and type of particles using the method illustrated in FIG. 7. Step S301 through Step S304 of FIG. 7 are identical to Step S201 through Step S204 in FIG. 6. Moreover, Step S309 through Step S311 of FIG. 7 are identical to Step S207 through Step S209 in FIG. 6. In Step S306, the evaluating portion 301 evaluates whether or not the estimated fluorescent band spectrum includes the flavin-derived fluorescent spectrum and the NADH-derived fluorescent spectrum. If the estimated fluorescent band spectrum includes both the flavin-derived fluorescent spectrum and the NADH-derived fluorescent spectrum, then, in Step S307, the evaluating portion 301 concludes that there is a high probability that the gas that is being tested includes a microorganism particle. If the estimated fluorescent band spectrum includes the flavin-derived fluorescent spectrum but does not include the NADH-derived fluorescent spectrum, then, in Step S308, the evaluating portion 301 concludes that a microorganism is included in the gas that is being tested, but that is the reliability of that conclusion is somewhat lower than in the case wherein both the flavin-derived fluorescent spectrum and the NADH-derived fluorescent spectrum are detected. Step S312 and Step S313 in FIG. 7 are identical to Step 5210 and Step 5211 in FIG. 6.

Other Examples

While there are descriptions of examples as set forth above, the descriptions and drawings that form a portion of the disclosure are not to be understood to limit the present disclosure. A variety of alternate examples and exemplary operating technologies should be obvious to those skilled in the art. For example, the location wherein the particle detecting device 1 according to the present example is not limited to being a clean room. Moreover, although in the example set forth above, the explanation was for an example wherein the fluorescent particle that is subject to detection is a microorganism particle that includes NADH and flavin, the fluorescent particle that is to be detected may instead be a non-microorganism particle. If here the non-microorganism particle emits fluorescence at a plurality of wavelengths, then fluorescent light at a wavelength that is distinct from that of the wavelength of Raman scattered light should be measured. In this way, the present disclosure should be understood to include a variety of examples, and the like, not set forth herein.

The invention claimed is:

1. A particle detecting device comprising:
 a light source that illuminates a fluid with an excitation beam;
 a fluorescence measuring instrument that measures light in a fluorescent band, which is produced in a region that is illuminated by the excitation beam; and
 an evaluating portion that evaluates whether or not the light that is measured by the fluorescence measuring instrument includes Raman-scattered light and florescent light, to evaluate that a fluorescent particle is included in the fluid if the evaluation is that the measured light includes florescent light, and to evaluate that the fluid does not include a fluorescent particle if the evaluation is that the measured light does not include fluorescent light, to evaluate that moisture is included in the fluid if there is an evaluation that the measured light includes Raman scattered light, and to evaluate that the fluid does not include moisture if there is an evaluation that the measured light does not include Raman scattered light.

2. The particle detecting device as set forth in claim 1, wherein:
 the fluorescence derives from flavin, and
 the fluorescent particle is a microorganism.

3. The particle detecting device as set forth in claim 1, wherein:
 if the light measured by the fluorescence measuring instrument includes flavin-derived fluorescence and Raman scattered light, the evaluating portion concludes that the fluid includes a microorganism.

4. The particle detecting device as set forth in claim 3, wherein:
 the microorganism is *Escherichia coli*.

5. The particle detecting device as set forth in claim 1, wherein:
 if the light measured by the fluorescence measuring device includes a Raman scattered light and does not include flavin-derived fluorescence, the evaluating portion concludes that moisture is included in the fluid and that a microorganism particle is not included.

6. The particle detecting device as set forth in claim 1, wherein:
 the fluid is air that has been subjected to steam sterilization.

7. The particle detecting device as set forth in claim 1, wherein:
 the Raman scattered light has a wavelength of 460 nm.

8. The particle detecting device as set forth in claim 1, wherein:
 the evaluating portion evaluates whether or not the light measured by the fluorescence measuring instrument includes Raman scattered light and florescent light, based on a spectrum of light measured by the fluorescence measuring instrument.

9. The particle detecting device as set forth in claim 8, wherein:
 the evaluating portion calculates the spectrum based on intensity of light at a plurality of wavelengths, measured by the fluorescence measuring instrument.

10. The particle detecting device as set forth in claim 1, further comprising:
 a Mie scattered light measuring instrument that measures Mie scattered light that is produced in the region that is illuminated by the excitation beam, wherein:
 if Mie scattered light is measured by the Mie scattered light measuring instrument and no light of a fluorescent band is measured by the fluorescence measuring instrument, the evaluating portion concludes that the fluid includes a non-fluorescent particle.

11. A particle detecting method, including:
 illuminating a fluid by a light source with an excitation beam;
 measuring, by a fluorescence measuring instrument, light in a fluorescent band, which is produced in a region that is illuminated by the excitation beam; and
 evaluating by an evaluating portion whether or not the light that is measured by the fluorescence measuring instrument includes Raman-scattered light and florescent light, to evaluate that a fluorescent particle is included in the fluid if the evaluation is that the measured light includes florescent light, and to evaluate that the fluid does not include a fluorescent particle if the evaluation is that the measured light does not include fluorescent light, to evaluate that moisture is included in the fluid if there is an evaluation that the measured light includes Raman scattered light, and to evaluate that the fluid does not include moisture if there is an evaluation that the measured light does not include Raman scattered light.

12. The particle detecting method as set forth in claim 11, wherein:
 the fluorescence derives from flavin, and the fluorescent particle is a microorganism.

13. The particle detecting method as set forth in claim 11, further comprising:
 concluding that the fluid includes a microorganism if the light measured includes flavin-derived fluorescence and Raman scattered light.

14. The particle detecting method as set forth in claim 13, wherein:
 the microorganism is *Escherichia coli*.

15. The particle detecting method as set forth in claim 11, including:
 concluding that moisture is included in the fluid and that a microorganism particle is not included if the light measured includes a Raman scattered light and does not include flavin-derived fluorescence.

16. The particle detecting method as set forth in claim 11, wherein:
 the fluid is air that has been subjected to steam sterilization.

17. The particle detecting method as set forth in claim 11, wherein:
 the Raman scattered light has a wavelength of 460 nm.

18. The particle detecting method as set forth in claim 11, wherein:
 whether or not the light measured includes Raman scattered light and florescent light is evaluated based on a spectrum of light measured by the fluorescence measuring instrument.

19. The particle detecting method as set forth in claim 18, wherein:
the spectrum is calculated based on intensity of light at a plurality of wavelengths.

20. The particle detecting method as set forth in claim 11, further comprising:
measuring, by a Mie scattered light measuring instrument, Mie scattered light that is produced in the region that is illuminated by the excitation beam, wherein:
the evaluating portion concludes that the fluid includes a non-fluorescent particle if Mie scattered light is measured and no light of a fluorescent band is measured.

* * * * *